(12) United States Patent
Chapman

(10) Patent No.: US 8,347,887 B2
(45) Date of Patent: Jan. 8, 2013

(54) DEVICES AND METHODS FOR REVERSAL OF PERMANENT STERILIZATION

(75) Inventor: Kelly Ann Chapman, Altadena, CA (US)

(73) Assignee: AMS Research Corporation, Minnetonka, MN (US)

( * ) Notice: Subject to any disclaimer, the term of this patent is extended or adjusted under 35 U.S.C. 154(b) by 330 days.

(21) Appl. No.: 12/643,590

(22) Filed: Dec. 21, 2009

(65) Prior Publication Data

US 2010/0160936 A1  Jun. 24, 2010

Related U.S. Application Data

(60) Provisional application No. 61/140,142, filed on Dec. 23, 2008.

(51) Int. Cl.
*A61F 6/06* (2006.01)
*A61B 17/08* (2006.01)

(52) U.S. Cl. ........................................ 128/830; 606/153

(58) Field of Classification Search .......... 128/830–833; 606/150, 153, 215, 216; 604/164.03, 164.06, 604/164.01
See application file for complete search history.

(56) References Cited

U.S. PATENT DOCUMENTS

| | | | |
|---|---|---|---|
| 4,245,623 A | 1/1981 | Erb | |
| 4,682,592 A | 7/1987 | Thorsgard | |
| 6,068,637 A * | 5/2000 | Popov et al. | .................. 606/159 |
| 6,096,052 A | 8/2000 | Callister et al. | |
| 6,176,240 B1 | 1/2001 | Nikolchev et al. | |
| 6,432,116 B1 | 8/2002 | Callister et al. | |
| 6,526,979 B1 | 3/2003 | Nikolchev et al. | |
| 6,634,361 B1 | 10/2003 | Nikolchev et al. | |
| 6,684,884 B2 | 2/2004 | Nikolchev et al. | |
| 6,705,323 B1 | 3/2004 | Nikolchev et al. | |
| 6,709,667 B1 | 3/2004 | Lowe et al. | |
| 6,763,833 B1 | 7/2004 | Khera et al. | |
| 7,073,504 B2 | 7/2006 | Callister et al. | |
| 7,220,414 B2 | 5/2007 | Brocchini et al. | |
| 7,237,552 B2 | 7/2007 | Khera et al. | |
| 7,398,780 B2 | 7/2008 | Callister et al. | |
| 7,428,904 B2 | 9/2008 | Nikolchev et al. | |
| 7,506,650 B2 | 3/2009 | Lowe et al. | |
| 7,591,268 B2 | 9/2009 | Lowe et al. | |
| 2002/0013589 A1 | 1/2002 | Callister et al. | |
| 2003/0029457 A1 | 2/2003 | Callister et al. | |
| 2005/0081862 A1 | 4/2005 | Callister et al. | |
| 2005/0131431 A1 * | 6/2005 | Copa et al. | .................... 606/150 |
| 2007/0055259 A1 * | 3/2007 | Norton et al. | .................... 606/79 |
| 2008/0039828 A1 * | 2/2008 | Jimenez et al. | ................. 606/13 |
| 2008/0135054 A1 | 6/2008 | Callister et al. | |
| 2008/0178890 A1 | 7/2008 | Townsend et al. | |
| 2008/0308110 A1 | 12/2008 | Callister et al. | |

* cited by examiner

*Primary Examiner* — Kevin C Sirmons
*Assistant Examiner* — Ophelia A Hawthorne
(74) *Attorney, Agent, or Firm* — Kimberly K. Baxter; Gregory L. Koeller

(57) ABSTRACT

An anastomosis device and related methods of using said device for reversing a female sterilization procedure. The anastomosis device can include a tissue approximation structure allowing for grasping and approximation of proximal and distal tube stumps remaining from the sterilization procedure so as to restore a lumen defined by the fallopian tubes for subsequent passage of reproductive cells. The anastomosis device can comprise a catheter body that is advanced through the reproductive tract, past the uterus and into the proximal stump. A flexible guidewire can guide a tissue approximation structure to the proximal stump wherein a set of proximal approximating structures are extended to grasp the proximal stump. The tissue approximation structure is then advanced into the distal stump wherein a set of distal approximating structures grasp the distal stump and cause the proximal and distal stumps to be brought into contact so as to commence biological healing.

17 Claims, 8 Drawing Sheets

DEVICES AND METHODS FOR REVERSAL OF PERMANENT STERILIZATION

PRIORITY CLAIM

The present application claims priority to U.S. Provisional Application Ser. No. 61/140,142, filed Dec. 23, 2008 and entitled "ANASTOMOSIS FOR REVERSAL OF PERMANENT STERILIZATION", which is herein incorporated by reference in its entirety.

FIELD OF THE DISCLOSURE

The invention relates to the reversal of permanent sterilization. More specifically, the present invention is directed to apparatus and related methods for reversing permanent blockage or severance of the fallopian tube so as to allow a patient to regain fertility or in response to a complication arising from permanent sterilization.

BACKGROUND OF THE DISCLOSURE

Conventional contraceptive strategies generally fall within three categories: physical barriers, drugs and surgery. While each have certain advantages, they also suffer from various drawbacks. Barriers such as condoms and diaphragms are subject to failure due to breakage, displacement and misuse. Drug strategies, such as the pill and Norplant™, which rely on artificially controlling hormone levels, suffer from known and unknown side-effects from prolonged use. Finally, surgical procedures, such as tubal ligation and vasectomy, involve the costs and attendant risks of surgery, and are frequently not reversible.

In response to the aforementioned difficulties and inefficiencies of conventional contraceptive strategies, the Ovion Eclipse permanent sterilization product was developed and is expected to be available in 2008 from American Medical Systems of Minnetonka, Minn. Fundamental aspects of the Eclipse product are described within U.S. Pat. Nos. 6,096,052 and 6,432,116, each of which is herein incorporated by reference in its entirety. Generally, the Eclipse product comprises a mesh member that is transversely disposed within the fallopian tube using a suitable delivery system such as, for example, a delivery catheter or a conventional balloon catheter. Once positioned within the fallopian tube, the mesh member is permeable to allow for tissue ingrowth, or epithelialization, such that after a period of time, a tissue impregnated mesh member eventually fully occludes the fallopian tube. Through the minimally invasive nature of the Eclipse product, implantation of the device can be accomplished in a single office visit with little or no discomfort.

While the Eclipse product provides an effective and permanent method of contraception, there exists circumstances in which a patient may wish to reverse the procedure and conceive a child. While the prior patents disclose the use of conventional atherectomy devices, lasers, balloon catheters and plugs secured to the mesh member, there remains the opportunity to further improve upon the ability to reverse the contraceptive effects of the Eclipse device.

SUMMARY OF THE DISCLOSURE

The present disclosure provides an anastomosis device and related methods of using said anastomosis device for reversing a sterilization procedure within a patient's fallopian tube. More specifically, the present disclosure teaches the use of an anastomosis device having a tissue approximation structure allowing for grasping and approximation of proximal tube stumps and distal tube stumps remaining from the sterilization procedure so as to restore a lumen defined by the fallopian tubes for subsequent passage of reproductive cells. Generally, the anastomosis device can comprise a catheter body that is advanced through the reproductive tract, past the uterus and into the proximal stump. The anastomosis device can include a flexible guidewire with a radiopaque tip viewable with a suitable medical imaging system such as, for example, a fluoroscopic imaging system. Using the medical imaging system, the guidewire can be used to deliver the tissue approximation structure to the proximal stump such that a set of proximal approximating structure can be extended to grasp the proximal stump. The tissue approximation structure can then be advanced into the distal stump wherein a set of distal approximating structures can grasp the distal stump and cause the proximal and distal stumps to be brought into contact so as to commence biological healing and restoration of the lumen defined by the fallopian tube. In some embodiments, an inflation balloon can be inflated between the proximal and distal tissue approximation structures to define and maintain the lumen during the healing process.

In one aspect, the present disclosure is directed to an anastomosis device for grasping and retaining proximal and distal tube stumps remaining from a female sterilization procedure in which a reproductive lumen defined by a fallopian tube has been blocked or severed. The anastomosis device can comprise a catheter body having an actuatable tissue approximation structure in which proximal and distal sets of approximation members can be extended outward to grasp and capture the proximal and distal tube stumps. The anastomosis device can place the proximal and distal tube stumps in contact with each other such that biological healing of the tube stumps is commenced wherein the lumen defined by the fallopian tube is restored. The catheter body and tissue approximation structure are generally constructed of flexible materials such that the catheter body and tissue approximation structure can remain in place during a healing period while a patient is able to perform typical daily activities.

In another aspect, the present disclosure is directed to a method of reversing a female sterilization procedure. Generally, the method can comprise positioning an anastomosis device proximate a proximal tube stump remaining from the severing or blocking of a reproductive lumen defined by a fallopian tube. The method can further comprise actuating a tissue approximation structure such that proximal tissue approximation members are extended from a catheter body to grasp the proximal tube stump. The method can further comprise advancing the tissue approximation structure into the distal tube stump wherein distal tissue approximation structures are extended from the catheter body to grasp the distal tube stump. The method can further comprise positioning the proximal and distal tube stumps in direct contact to commence biological healing. The method can further comprise retaining the proximal and distal tube stumps in contact during a healing period. The method can further comprise defining a lumen at the point of contact between the proximal and distal tube stumps during the healing period.

The above summary of the invention is not intended to describe each illustrated embodiment or every implementation of the present invention. The Figures and the detailed description that follow more particularly exemplify these embodiments.

BRIEF DESCRIPTION OF THE FIGURES

The invention may be more completely understood in consideration of the following detailed description of various embodiments of the invention in connection with the accompanying drawings, in which.

Figure 1:
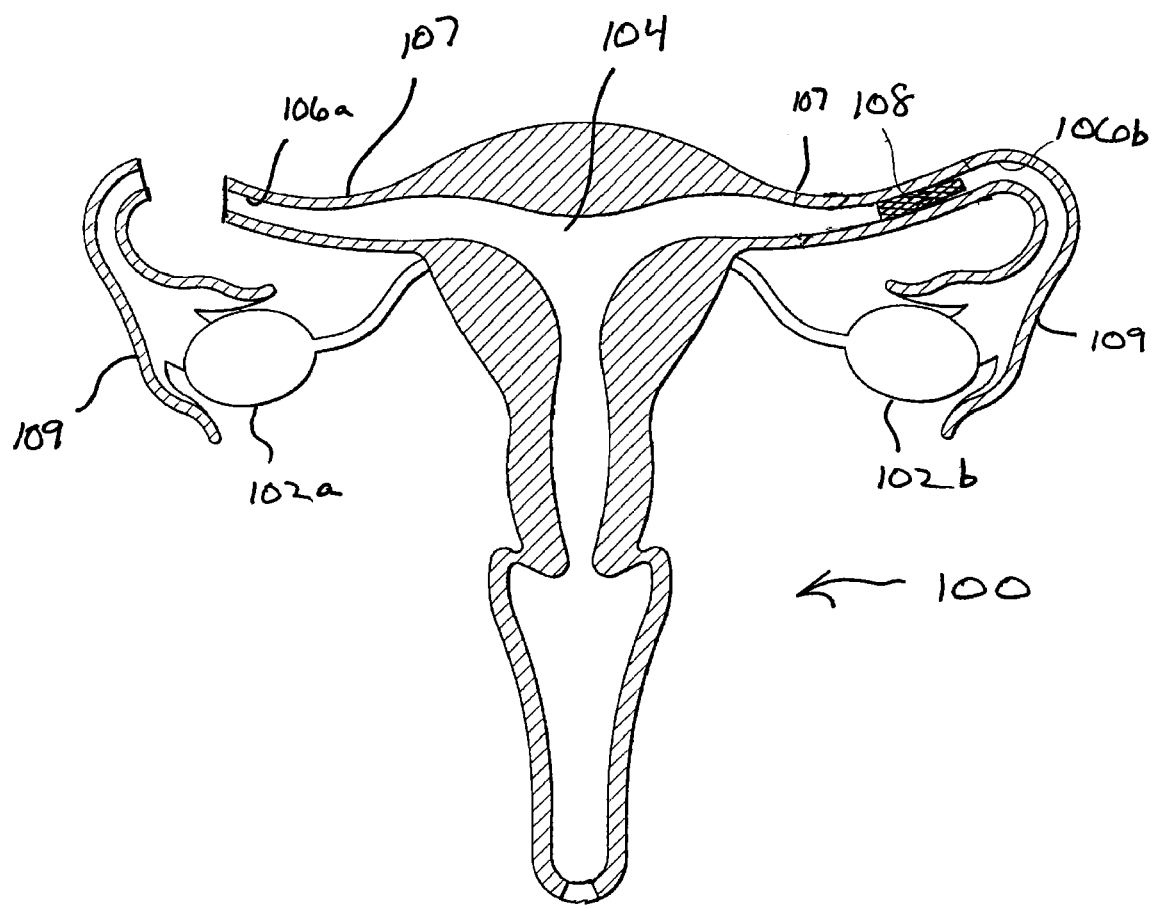
FIG. 1 is an illustration of a female reproductive tract in which a traditional sterilization procedure has severed a first fallopian tube while a mesh occluding member has been positioned within a second fallopian tube so as to accomplish female sterilization.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE FIGURES

As illustrated in FIG. 1, a female's reproductive tract 100 generally comprises a pair of ovaries 102a, 102b operably connected to a uterus 104 with fallopian tubes 106a, 106b. In some forms of conventional female sterilization as shown with reference to fallopian tube 106a, the fallopian tube 106a can be severed so as destroy the operable connection between ovary 102a and the uterus 104. In some instances, conventional sterilization procedures including, for example, tubal ligation involving cauterizing, cutting and/or removing portions of the body lumen, which can result in very small portions of the lumen, referred to as proximal stump 107 and distal stump 109 remaining available for reconnection using microsurgery techniques. In an alternative form of female sterilization as shown with reference to fallopian tube 106b, an occlusion member 108 can be positioned so as to occlude and physically block the fallopian tube 106b using ingrown tissue so as to occlude or physically block the fallopian tube 106b. Using occlusion member 108, the lumen remains essentially intact such that proximal stump 107 and distal stump 109 remain at a maximum possible length. Regardless of the particular method by which female sterilization is performed, the passage of reproductive cells through the lumen defined by the fallopian tubes 106a, 106b is prevented, either by destroying the integrity of the lumen or by physically blocking the lumen, such that the potential for pregnancy is eliminated.

In the event that a patient chooses to subsequently reverse either of the sterilization procedures illustrated in FIG. 1, the use of occlusion member 108 can provide beneficial in that the physical blocking of fallopian tube 106b does not compromise or destroy the integrity of the body lumen. Increasing the lengths of proximal stump 107 and distal stump 109 available for possible reconnection increases overall success rates for reversing sterilization. By physically blocking the body lumen with occlusion member 108 as opposed to severing the body lumen, there remains enough of the proximal stump 107 and distal stump 109 such that overall success rates for the reversal process are much higher.

Figure 2:
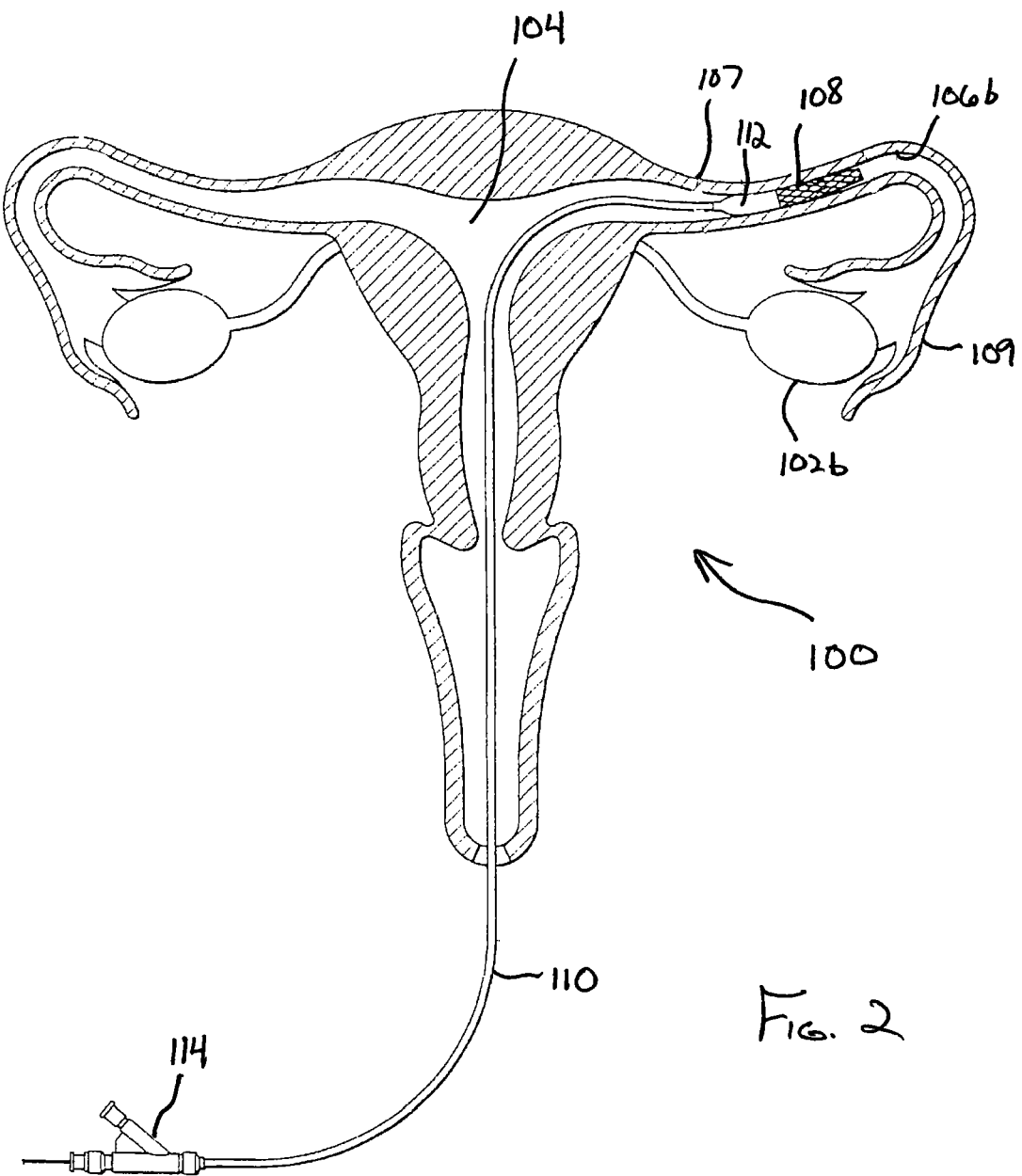
FIG. 2 is an illustration of an insertion procedure for positioning the mesh occluding member shown in FIG. 1.

When the process of physically blocking the fallopian tube is desired, one presently preferred embodiment for occlusion member 108 can comprise the Ovion Eclipse device as previously described. Generally, the occlusion member 108 can comprise an intertwined mesh formed by strands of a biocompatible material. At a time of original implantation within the fallopian tube 106b, the occlusion member 108 can resemble a tubular member having a pair of opposed ends with a lumen extending therein. So as to effectively accomplish implantation and positioning within the fallopian tube 106, the occlusion member 108 can be provided in a reduced diameter configuration. Once positioned within fallopian tube 106b using fluoroscopic, hysteroscopic, or ultrasonic visualization, the occlusion member 108 can be deformed to an expanded diameter using a suitable expanding element such as, for example, a balloon catheter 110 as illustrated in FIG. 2. Generally, the occlusion member 108 can be placed over an end balloon 112, which can be inflated with an inflation fluid administered through an adapter 114 on the balloon catheter 110. When expanded within the fallopian tube 106, the occlusion member 108 can have expanded transverse dimensions from about 0.1 mm to about 5 mm. In some instances, occlusion member 108 can comprise a self-expanding element or can include a variety of complimentary or alternative mechanical, adhesive or other anchoring means to originally secure the occlusion member 108 within the reproductive lumen. Over a period of a week or more, epithelial cells lining the lumen will proliferate, growing around the open framework and within the mesh openings of occlusion member 108, thereby permanently securing the occlusion member 108 within the lumen and occluding the fallopian tube 106b.

Figure 3:
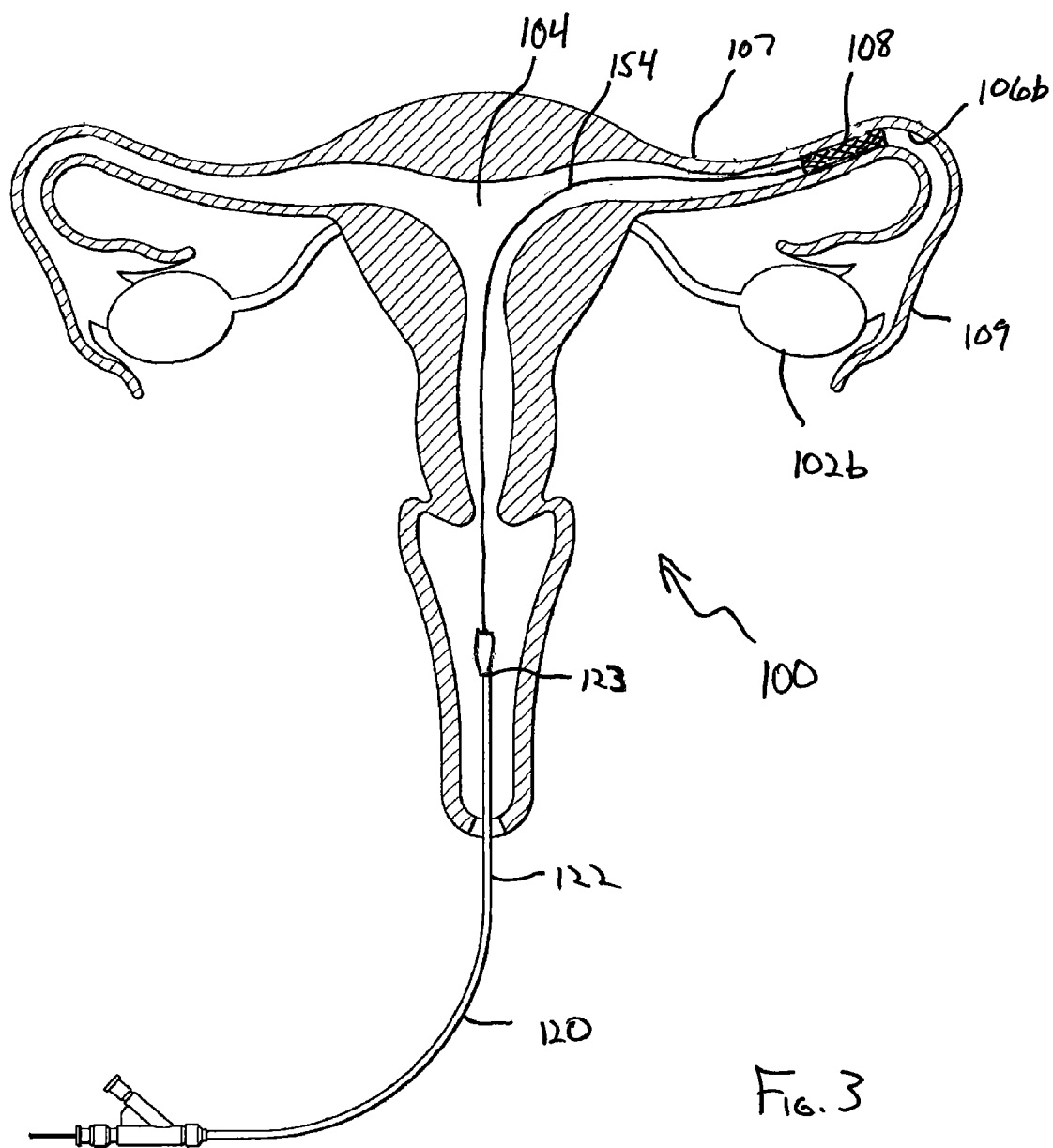
FIG. 3 is an illustration of a first approximation step for reestablishing the integrity of the fallopian tube so as to reestablish the reproductive ability of a patient.
Figure 4:
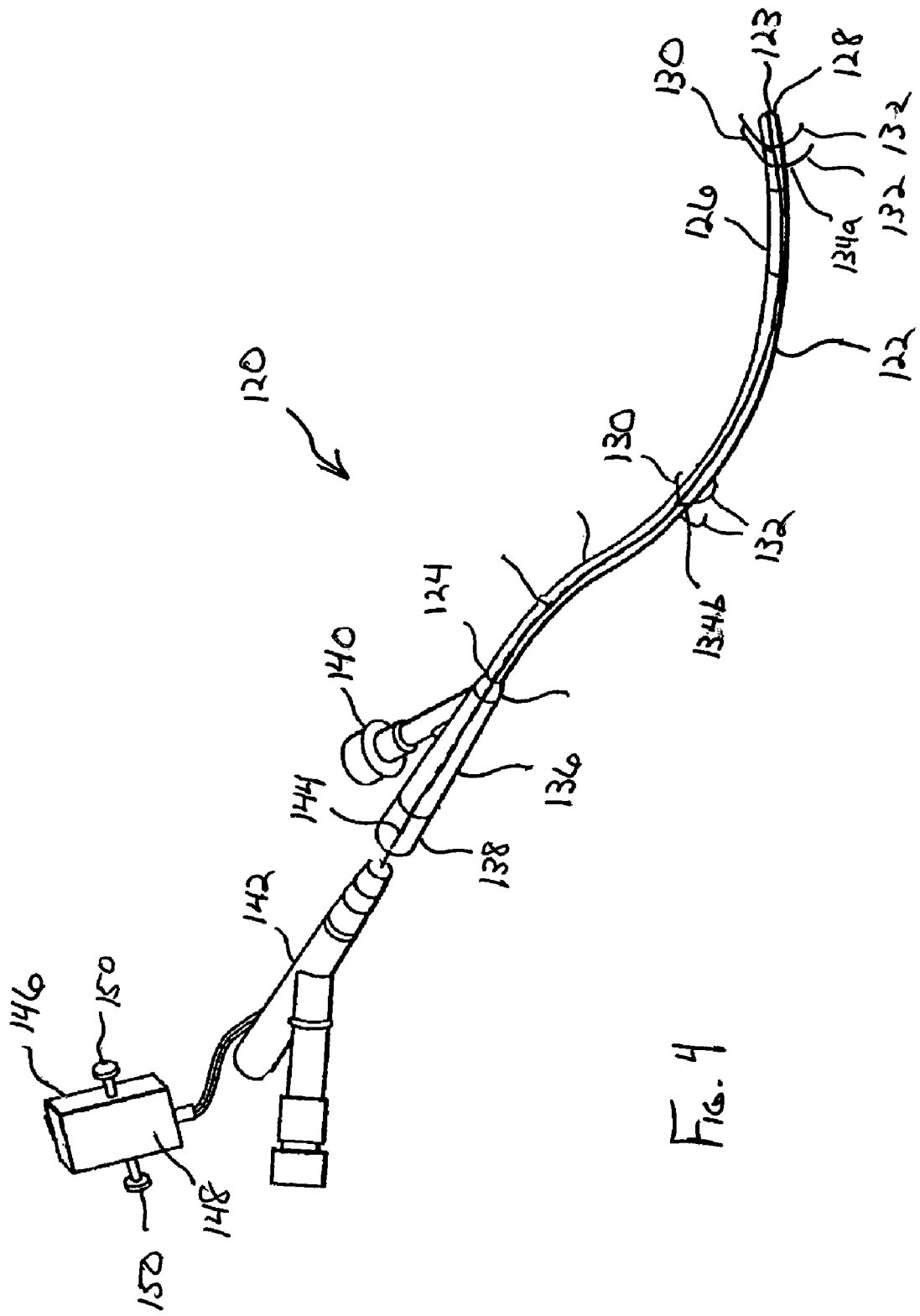
FIG. 4 is a perspective view of a representative embodiment of an anastomosis device for use in reestablishing the integrity of the fallopian tube.

As illustrated in FIG. 3, an anastomosis device 120 can be delivered to the site of occlusion member 108 physically blocking a body lumen. Referring to FIG. 4, anastomosis device 120 can comprise a catheter body 122, a distal end portion 123, a proximal end portion 124, a balloon 126, a drainage aperture 128 and a tissue approximating structure 130. Tissue approximating structure 130 can comprise a single structure or multiple structures generally positioned along the catheter body 122 between the distal end portion 123 and the proximal end portion 124. With the exception of the tissue approximation structure 130, anastomosis device 120 can similarly resemble both the structural and fabrication of a conventional Foley catheter that is typically inserted into a patient's bladder to drain urine.

As shown, one exemplary embodiment of tissue approximating structure 130 includes multiple sharp elongate metal tines 132 that can extend from and retract into catheter body 122 at a location that allows contact and optional penetration of adjacent tissue structures. For example, the tissue approximating structure 130 can be positioned within a patient to allow contact and optional penetration of the fallopian tube 106. In some embodiments, tissue approximating structure 130 can specifically include two sets of elongated structures, which are deployable or otherwise moveable in opposed directions from each other. The elongated structures can be rigid or semi-rigid tines, needles, or the like, having a straight or curved configuration. In some embodiments, the elongated structures can include a sharp pointed tip to penetrate into the body lumen or other tissue that can be brought into contact or held together by devices or methods described herein.

Referring to FIG. 4, anastomosis device 120 can include a first or distal set of tissue approximating structures 134a located on the distal side of the balloon 126 and positioned to extend through apertures in the hollow catheter body 122. Anastomosis device 120 can further include a second or proximal set of tissue approximating structures 134b that are similarly positioned to extend through apertures in hollow catheter body 122 and that are located on the proximal side of the tissue approximating structures 134a. Each of the two sets of tissue approximating structures 134a, 134b can be extendable at the same time or may be controllable independently and remotely relative to each other, such as through the operation of an actuating mechanism. A wide variety of actuating mechanisms may be used, such as a wire or shaft connected to the tissue approximating that runs through or along the length of the catheter body, some examples of which will be described in further detail below.

Referring again to FIG. 4, proximal end portion 124 of the anastomosis device 120 comprises a main body portion 136 that extends from proximal end portion 124 of catheter body 122. Main body portion 136 extends generally in the direction of the length of catheter body 122 and can have an increased diameter than catheter body 122. A port 140 can extend or otherwise protrude from main body portion 136 and can connect to a lumen (not shown) such as, for example, an inflation lumen for balloon 126 or a drainage lumen operably connected to drainage aperture 128. Anastomosis device 120 can further include one or more additional extensions 142 extending from the end 138 of the main body portion 136 opposite the end attached to catheter body 122. Extension 142 can include an extension port 143 that can substantially resemble port 140 in that extension portion 143 can be similarly utilized with a lumen such as, for example, an inflation lumen for balloon 126 or a drainage lumen operably connected to drainage aperture 128. Extension 142 can attach to main body portion 136 using suitable connections including, for example, mechanical configurations including snap-fit or threaded designs, or using adhesives or the like. In some embodiments, extension 142 can be integrally fabricated with main body 136.

Anastomosis device 120 can further include at least one actuating wire 144 that extends through the interior portion of catheter body 122, such as within the wall of catheter body 122 or within an open channel through catheter body 122. Actuating wire 144 is attached to an actuating mechanism 146 that is used for extending and retracting tissue approximating structures 130. As shown, actuating wire 144 can extend generally along the length of catheter body 122 from tissue approximating structures 130, through proximal end portion 124, and into extension 142. Actuation wire 144 can then communicate with or be attached to actuating mechanism 146, one exemplary embodiment of which is illustrated as extending from main body portion 136.

While actuating wire 144 is illustrated as a single wire, actuating wire 144 can comprise a series or bundle of wires that each activate one set or more than one set of tissue approximating structures 130. Further, actuating wire 144 may not actually be a wire, but may instead have a different structure or configuration, depending on the tissue approximating structure 130 used. That is, if the tissue approximating structure 130 is actuated by a mechanism other than a wire, (e.g., fluid or air pressure), a corresponding actuating device or structure will be used instead of an actuating wire or wires. For one specific example, actuating wire 144, can take the configuration of a tube if the corresponding tissue approximating structure 130 is an inflatable balloon. Further, it is contemplated that the tissue approximating structure 130 or structures can be attached to an actuating mechanism 146 in a number of different ways, depending on the configuration of the tissue approximating structures 130 and the corresponding devices or structures used for activation of those tissue approximating structures 130.

In one exemplary embodiment, actuating mechanism 146 can comprise an actuator body 148 and two extending control knobs 150. Internal componentry within actuator body 148 can include a wide variety of configurations, but generally involves a connection between the actuating mechanism 146 such as, for example, actuating wire 144 from the tissue approximating structures 130 to the control knobs 150 of the actuating mechanism 146. Actuating mechanism 146 can include a variety of external control configurations in place of or in addition to control knobs 150 including, for example, levers, pins, buttons, or the like, which are able to be physically manipulated to maneuver the tissue approximating structures 130.

Figure 5:
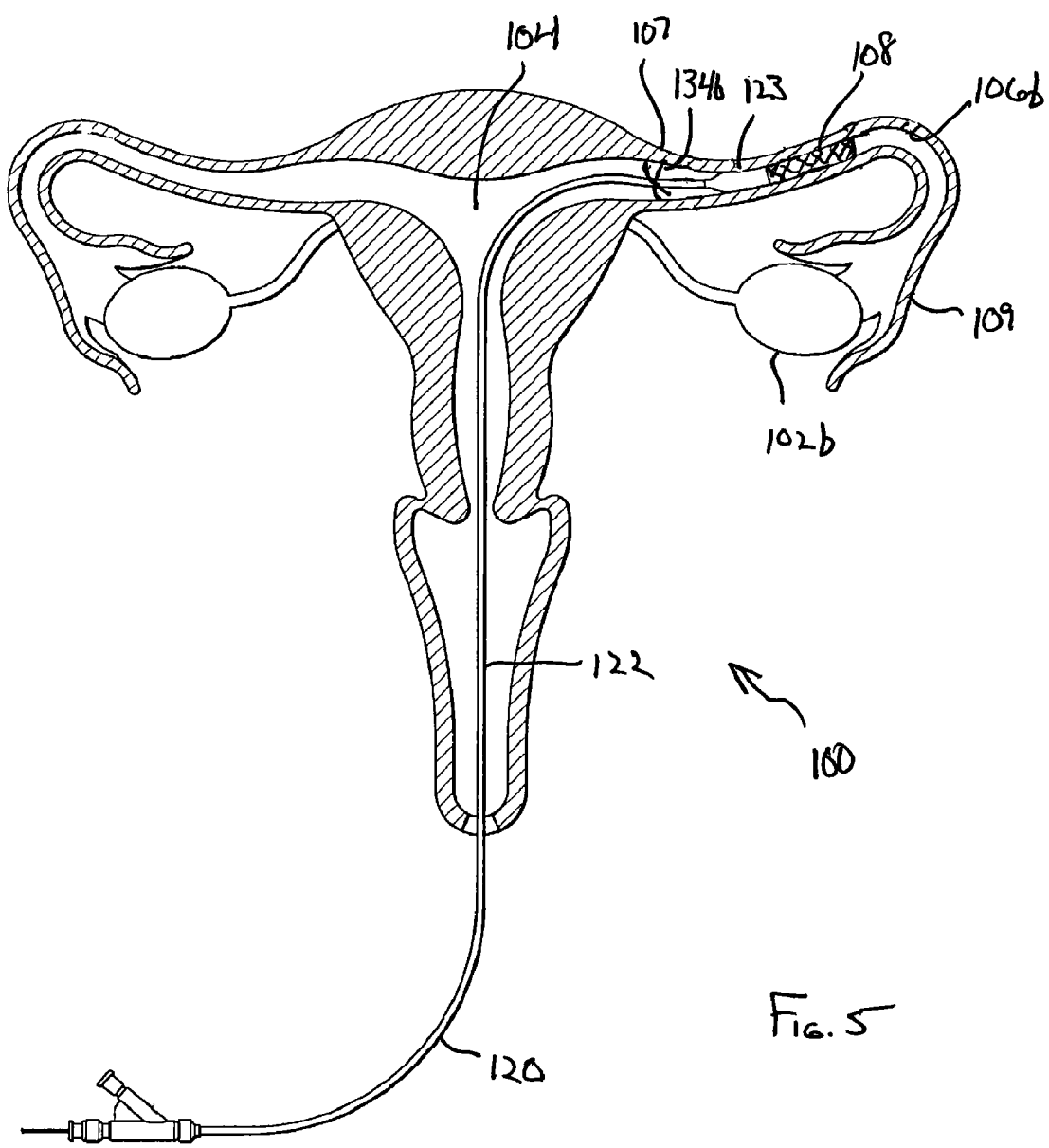
FIG. 5 is an illustration of a second step for reestablishing the integrity of the fallopian tube so as to reestablish the reproductive ability of a patient.

Reversal of the sterilization methods illustrated generally in FIG. 1 can be accomplished by first positioning the anastomosis device 120 and more specifically the distal end portion 123 within the proximal stump 107. Generally, catheter body 122 is advanced into the reproductive tract 100 such that distal end portion 123 enters the proximal stump 107. In some embodiments, a guidewire 154 can be introduced through port 140 or extension port 143 and advanced to the proximal stump 107 using a suitable imaging technology including, for example, a fluoroscopic imaging system, to precisely position the guidewire as shown in FIG. 3. Catheter body 122 can then be advanced over the guidewire to verify precise positioning of the distal end portion 123. Once the distal end portion 123 has been positioned within the proximal stump 107 as shown in FIG. 5, a medical professional can advance the tissue approximation structures 130 to distal end portion 123 wherein actuating mechanism 146 can cause tissue approximating structures 134b to extend such that they grasp and capture the proximal stump 107.

Figure 5A:
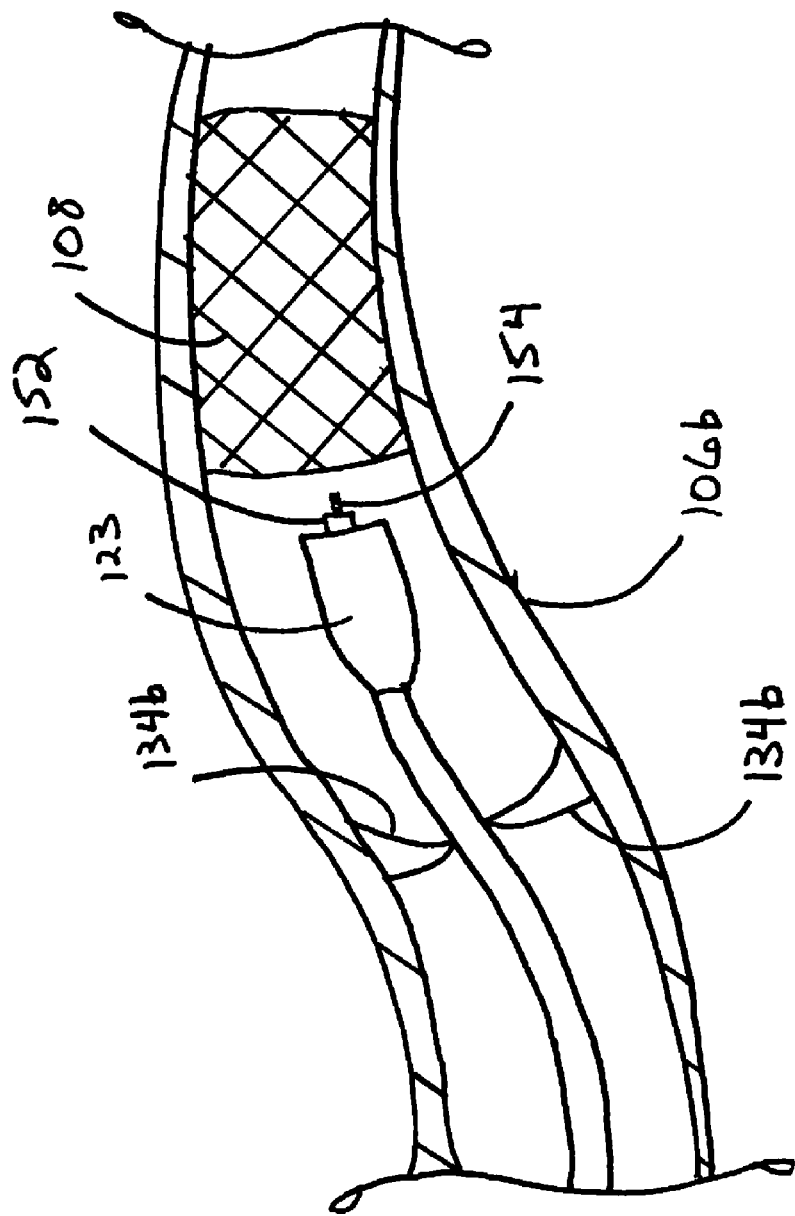
FIG. 5a is an illustration of a cutting step for removing an occlusion member from a fallopian tube so as to reestablish the reproductive ability of a patient.
Figure 6:
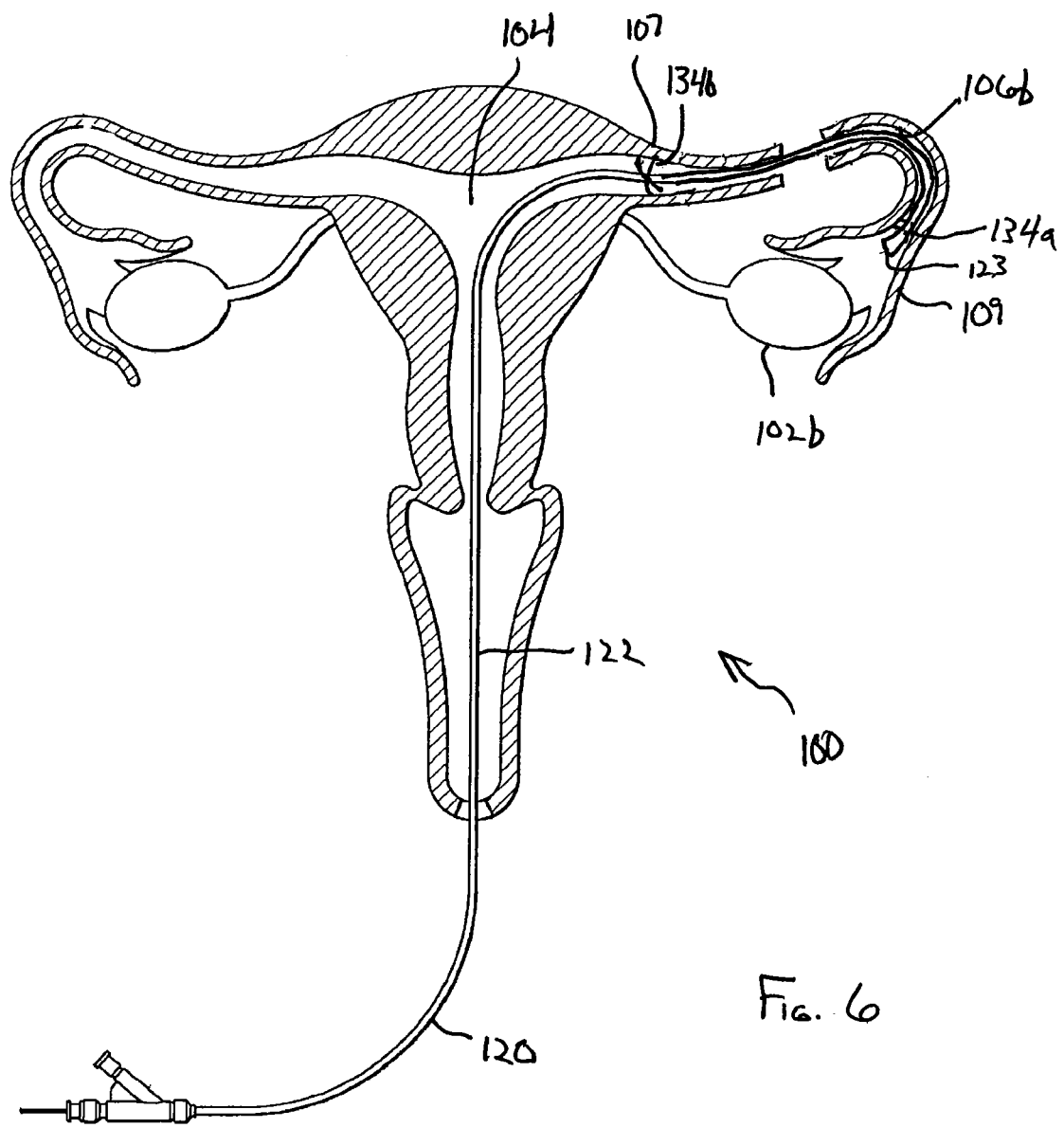
FIG. 6 is an illustration of a third step for reestablishing the integrity of the fallopian tube so as to reestablish the reproductive ability of a patient.
Figure 7:
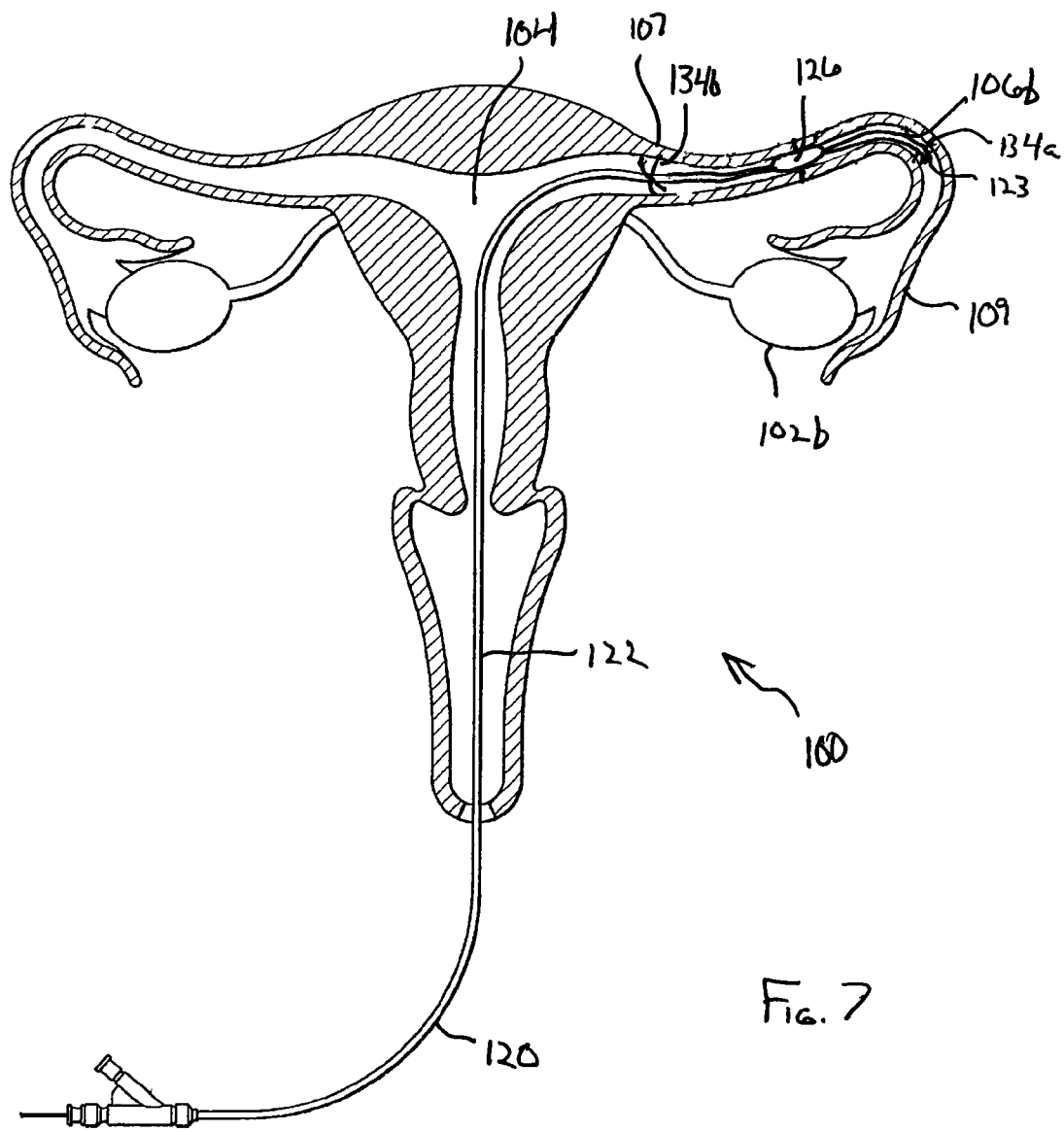
FIG. 7 is an illustration of a fourth step for reestablishing the integrity of the fallopian tube so as to reestablish the reproductive ability of a patient.

In the event that the integrity of the fallopian tube has been severed or destroyed as shown with fallopian tube 106a, the tissue approximating structures 130 and, if used, the guidewire, can be directed through the proximal stump 107 and into the distal stump 109. kim If instead, occlusion member 108 has been utilized to physically block the fallopian tube as shown with fallopian tube 106b, a cutting member 152 such as, for example, a rotary cutter, a drill or a laser-based cutter 154 can be advanced through the catheter body 122 such that it is positioned proximate the occlusion member 108 as shown in FIG. 5a. Depending upon the configuration of the cutting member, the occlusion member 108 can be essentially drilled through to reopen the lumen or, alternatively, the fallopian tube 106b can be severed on both sides of the occlusion member 108 so as to physically remove the occlusion section of the lumen. If fallopian tube 106b is severed to remove the occlusion member 108, the guidewire can then be advanced into the distal stump 109 as described previously to provide a pathway for advancement of the tissue approximation structure 130.

Once the distal end portion 123 has been positioned within the distal stump 109, a medical professional using actuating mechanism 146 can cause the tissue approximating structures 134a to extend such that they grasp and capture the distal stump 109. With the distal stump 109 captured, the medical professional can cause the tissue approximating structures to be withdrawn toward the distal end portion 123 such that the distal stump 109 is pulled into proximate contact with the proximal stump 107. With the proximal stump 107 and distal stump 109 held in contact, biological healing of the proximal stump 107 and distal stump 109 commences wherein the integrity of the fallopian tube is restored. Balloon 126 can be inflated between the tissue approximating structures 134a, 134b so as to maintain the lumen during the healing process. During the healing process, which can take a number of weeks, the catheter body 120 can remain in position so as to allow the patient to perform everyday activities while physically retaining the proximal stump 107 and distal stump 109 in physical contact. Through the use of tissue approximating structure 130, restoration of the integrity of the fallopian tubes can be accomplished without the need for sutures which can require difficult and delicate procedures.

Although specific examples have been illustrated and described herein, it will be appreciated by those of ordinary skill in the art that any arrangement calculated to achieve the same purpose could be substituted for the specific example shown. This application is intended to cover adaptations or variations of the present subject matter. Therefore, it is intended that the invention be defined by the attached claims and their legal equivalents.

The invention claimed is:

1. A system for restoring a reproductive lumen, comprising:
   an elongate catheter body having a proximal end portion and a distal end portion;
   an inflatable balloon positioned along the elongate catheter body proximate the distal end portion;
   a distal set of tissue approximating structures positioned along the elongate catheter body between the balloon and the distal end portion;
   a proximal set of tissue approximating structures positioned along the elongate catheter body between the balloon and the proximal end portion;
   an actuating mechanism connected to distal and proximal sets of tissue approximating structures configured to independently control the tissue approximating structures and selectively move them relative to each other, and
   a cutting member selectively insertable through the elongate catheter body, such that the cutting member is adapted to clear an end obstruction in each of a pair of lumen stumps such that the reproductive lumen is restored following approximation of the lumen stumps.

2. The system of claim 1, further comprising:
   a main body portion extending from the proximal end portion; and
   a port extending from the main body portion, the port connecting to a lumen extending through the elongate catheter portion.

3. The system of claim 2, wherein the lumen is fluidly connected to the inflatable balloon.

4. The system of claim 2, wherein the lumen comprises a drainage lumen for draining bodily fluids through the main body portion.

5. The system of claim 1, wherein the actuating mechanism connects to the distal and proximal sets of tissue approximating structures via at least one actuating wire extending through the elongate catheter body.

6. The system of claim 5, wherein a first wire connects to the proximal set of tissue approximating structures and a second wire connects to the distal set of tissue approximating structures, and wherein the actuation mechanism independently extends and retracts the distal and proximal sets of tissue approximating structures using the first wire and the second wire.

7. The system of claim 1, wherein the distal set and the proximal set of tissue approximating structures comprise elongate metal tines that can selectively extend from and retract into the elongate catheter body.

8. The system of claim 1, wherein the cutting member is selected from the group consisting of: a rotary cutter, a drill, and a laser-based cutter.

9. A method for reversing a sterilization procedure, comprising:
   providing an anastomosis device including an elongate catheter body having a distal end portion, a proximal set of tissue approximating structures, and a distal set of tissue approximating structures;
   positioning the distal end portion in a proximal stump of a fallopian tube;
   extending the proximal set of tissue approximating structures to grasp the proximal stump;
   advancing the distal end portion into a distal stump of the fallopian tube;
   extending the distal set of tissue approximating structures to grasp the distal stump;
   pulling the proximal stump and the distal stump into physical contact to reestablish the fallopian tube; and
   holding the proximal stump and distal stump in contact with each other during a healing period for restoring physical integrity of the fallopian tube, the proximal stump and distal stump being held by the proximal and distal sets of tissue approximating structures respectively;
   positioning a cutting member proximate an occlusion member separating the proximal stump from the distal stump, and
   creating a path from the proximal stump to the distal stump.

10. The method of claim 9, further comprising:
    inserting a guidewire through a port on the anastomosis device;
    advancing the guidewire into the proximal stump;
    advancing the distal end portion over the guidewire and into the proximal stump.

11. The method of claim 10, further comprising:
    viewing the guidewire with an imaging system to precisely position the guidewire in the proximal stump.

12. The method of claim 9, wherein advancing the distal end portion into the distal stump, comprises:
    traversing a severed portion of the fallopian tube prior to directing the distal end portion into the distal stump.

13. The method of claim 9, wherein the step of creating a path from the proximal stump to the distal stump includes drilling through the occlusion member.

14. The method of claim 9, wherein the step of creating a path from the proximal stump to the distal stump includes severing the fallopian tube on both sides of the occlusion member and removing the occlusion member.

15. The method of claim 9, wherein the anastomosis device further comprises an inflatable balloon positioned proximate the distal end portion, the method further comprising:
    inflating the inflatable balloon within the fallopian tube where the proximal stump and the distal stump are being held in physical contact to maintain an opening in the fallopian tube while the proximal stump and the distal stump during the healing period.

16. A method for reversing a sterilization procedure, comprising:
    evaluating a fallopian tube to determine the type of sterilization procedure performed and the structural integrity of the fallopian tube;

providing an anastomosis device including an elongate catheter body having a distal end portion, a proximal set of tissue approximating structures, and a distal set of tissue approximating structures;

positioning the distal end portion in a proximal stump of a fallopian tube;

extending the proximal set of tissue approximating structures to grasp the proximal stump;

advancing the distal end portion into a distal stump of the fallopian tube;

extending the distal set of tissue approximating structures to grasp the distal stump;

pulling the proximal stump and the distal stump into physical contact to reestablish the fallopian tube; and holding the proximal stump and distal stump in contact with each other during a healing period for restoring physical integrity of the fallopian tube, the proximal and distal stumps being held by the proximal and distal sets of tissue approximating structures respectively.

17. The method of claim 16, further comprising:

positioning a cutting member proximate an occlusion member separating the proximal stump from the distal stump, and creating a path from the proximal stump to the distal stump.

* * * * *